United States Patent [19]

Lee et al.

[11] Patent Number: 5,104,795

[45] Date of Patent: Apr. 14, 1992

[54] SHORTENED PHOSPHOGLYCERATE KINASE PROMOTER

[75] Inventors: Jar-How Lee; Lindley Blair; Arnold Horwitz; Raju K. Koduri, all of Los Angeles, Calif.

[73] Assignee: Zoma Corporation, Berkeley, Calif.

[21] Appl. No.: 480,003

[22] Filed: Feb. 14, 1990

Related U.S. Application Data

[63] Continuation of Ser. No. 73,804, Jul. 13, 1987, abandoned, which is a continuation-in-part of Ser. No. 797,477, Nov. 13, 1985, abandoned.

[51] Int. Cl.$^5$ .................. C12P 21/02; C12N 15/11
[52] U.S. Cl. .................. 435/69.1; 435/172.3; 435/252.3; 435/255; 435/320.1; 536/27
[58] Field of Search .................. 435/69.1, 61.8, 69.2, 435/69.4, 172.3, 255, 256, 320.1; 536/27; 935/37, 20, 47, 48, 56, 60, 69

[56] References Cited

U.S. PATENT DOCUMENTS 4,615,974  10/1986  Kingsman et al. .................. 435/69.1

FOREIGN PATENT DOCUMENTS 0073635   3/1983   European Pat. Off. ......... 435/69.1
0077670   4/1983   European Pat. Off. ......... 435/69.1
84/04757  12/1984  European Pat. Off. ......... 435/69.1
0139501   5/1985   European Pat. Off. ......... 435/69.1
WO84/04538 11/1984 PCT Int'l Appl. .......... 435/69.1

OTHER PUBLICATIONS

Erhart et al. *J. Bact.* vol. 156 pp. 625–635 1983.
Edens et al. *Cell* vol. 37 pp. 629–633 1984.
Hitzeman et al. *Science* vol. 219 pp. 620–625 1983.
Smith et al. *Science* vol. 229 pp. 1219–1224 Sep. 1985.
Dobson, M. J. et al., Nucl. Acids Res. 10:2625–2637 (1982).
Tuite, M. F. et al., EMBO Journal 1:603–608 (1982).
Chen, C. Y. et al., Nucl. Acids Res. 12:8951–8970 (1984).
Hitzeman, R. A. et al., Res. Nucl. Acids. 10:7791–7808 (1982).
Chang, C. N. et al., Molec. Cell. Biol. 6:1812–1819 (1986).
Derynck, R. et al., Nucl. Acids Res. 11:1819–1837 (1983).
Dobson, M. J. et al., Nucl. Acids Res. 11:2287–2302 (1983).
Horwitz, A. H. et al., Proc. Natl. Acad. Sci U.S.A. 85:8678–8682 (1988).
Huang, S. et al., Biochem 26:8242–8246 (1987).
Kingsman, S. M. et al., Biotech Gen. Engin. Rev. 3:377–416 (1985).
Lee, J.-H. et al., Biochem 27:5101–5107 (1988).
Mellor, J. et al., Gene 33:215–226 (1985).
Rothstein, S. J. et al., Nature 308:662–665 (1984).

*Primary Examiner*—Robin L. Ieskin
*Attorney, Agent, or Firm*—Sterne, Kessler, Goldstein and Fox

[57] ABSTRACT

A shortened PGK promoter ranging from 165 to 404 base pairs of the Saccharomyces PGK promoter is taught. The promoter is operably linked to heterologous genes and improves the expression thereof relative to the full length PGK promoter.

12 Claims, 12 Drawing Sheets

SHORTENED PHOSPHOGLYCERATE KINASE PROMOTER

CROSS REFERENCE TO RELATED APPLICATION

This application is a continuation of application Ser. No. 07/073,804 filed Jul. 13, 1987, now abandoned, which is a continuation-in-part of 06/997/477, filed Nov. 13, 1985 now abandoned.

BACKGROUND OF THE INVENTION

1. Field of the Invention

This invention is in the field of genetic engineering. The invention is directed to a shortened phosphoglycerate kinase (PGK) promoter and the improvement it provides to the expression of polypeptides under its control. In addition, this invention is directed to the use of the shortened PGK promoter operably linked to a secretion signal that provides for improved secretion of the expressed proteins into the culture medium.

2. Background of the Invention

The glycolytic enzyme genes of *Saccharomyces cerevisae* encode some of the most abundant mRNA of protein species in the cell. The phosphoglycerate kinase (PGK) gene in the yeast genome has been extensively studied. Dobson et al., "Conservation of High Efficiency Promoter Sequences in *Saccharomyces cerevisae*," *Nucleic Acids Research*, 10: 2625-2637 (1982). The 5' control regions of the yeast glycolytic enzyme genes are particularly attractive for incorporation into yeast expression vectors as each gene encodes 1-5% of the total mRNA in protein. Further, the glycolytic genes are readily regulated by glucose. Thus, high level expression of a gene operably linked to the PGK promoter may be regulated by the simple control of the carbon source, glucose.

Researchers have identified approximately 1,500 nucleotides as the PGK 5' flanking region (the PGK promoter), derived from a 3 Kbp Hind III fragment. Using this full-length PGK promoter, the levels of heterologous protein produced under the control of the PGK promoter were not as high as expected for this promoter. Tuite et al., "Regulated High Efficiency Expression of Human Inteferon--Alpha in *Saccharomyces cerevisae*," EMBO Journal, 1: 603-608 (1982). Researchers have also reported that using the full length 5' DNA control regions of highly expressed yeast glycolytic genes, the protein levels produced were far less than that of the normal homologous gene product. In Chen et al., "Homologous v. Heterologous Gene Expression in the Yeast, *Saccharomyces cerevisae*," *Nucleic Acids Research*, 12: 8951-8970 (1984) the studies showed that the expression in yeast of heterologous genes adjacent to the PGK promoter on a high copy number plasmid vector were 15-50 times lower than the expression of the natural homologous gene on the same plasmid.

Applicants herein have discovered that using a PGK promoter with a shortened length of less than 500 base pairs improves the expression of polypeptides under its control. Thus, less time is required for transformants to appear, and there is an increase in polypeptide production.

SUMMARY OF THE INVENTION

According to the present invention, there is provided a shortened promoter of the PGK gene comprising less than 500 base pairs of the proximal end of the 5' region of the PGK gene, preferably, comprising the promoter sequence length of about 165 to about 404 base pairs of the proximal end of the 5' region of the PGK gene.

The invention also provides for a polynucleotide molecule expressible in a given host comprising the sequence of the shortened PGK promoter operably linked to a structural gene which may be homologous or heterologous to said host.

This invention further provides for the use of the shortened PGK promoter operably linked to a secretion signal that thus regulates the expression and improved secretion of the expressed polypeptide or protein into the culture medium.

The invention also provides for vehicles capable of replication and expression comprising said shortened PGK promoter operably linked to the structural gene, and also provides for hosts transformed with the vehicle.

In one embodiment of the invention disclosed and claimed herein, the shortened PGK promoter is used with a process for regulating yeast plasmid copy number by two selectable markers. The regulation of yeast plasmid copy number is based mostly on the strength of the promoters of the selectable marker genes; a strong promoter for the first selectable marker selects only for low copy number, whereas a weak promoter for the second selectable marker selects for high copy number. High-level expression of the structural gene linked to the shortened PGK promoter is dependent upon increasing the plasmid copy number to a high level. This process is particularly useful when high level expression of a gene product is lethal to host cells.

DEFINITIONS

Figure 1:
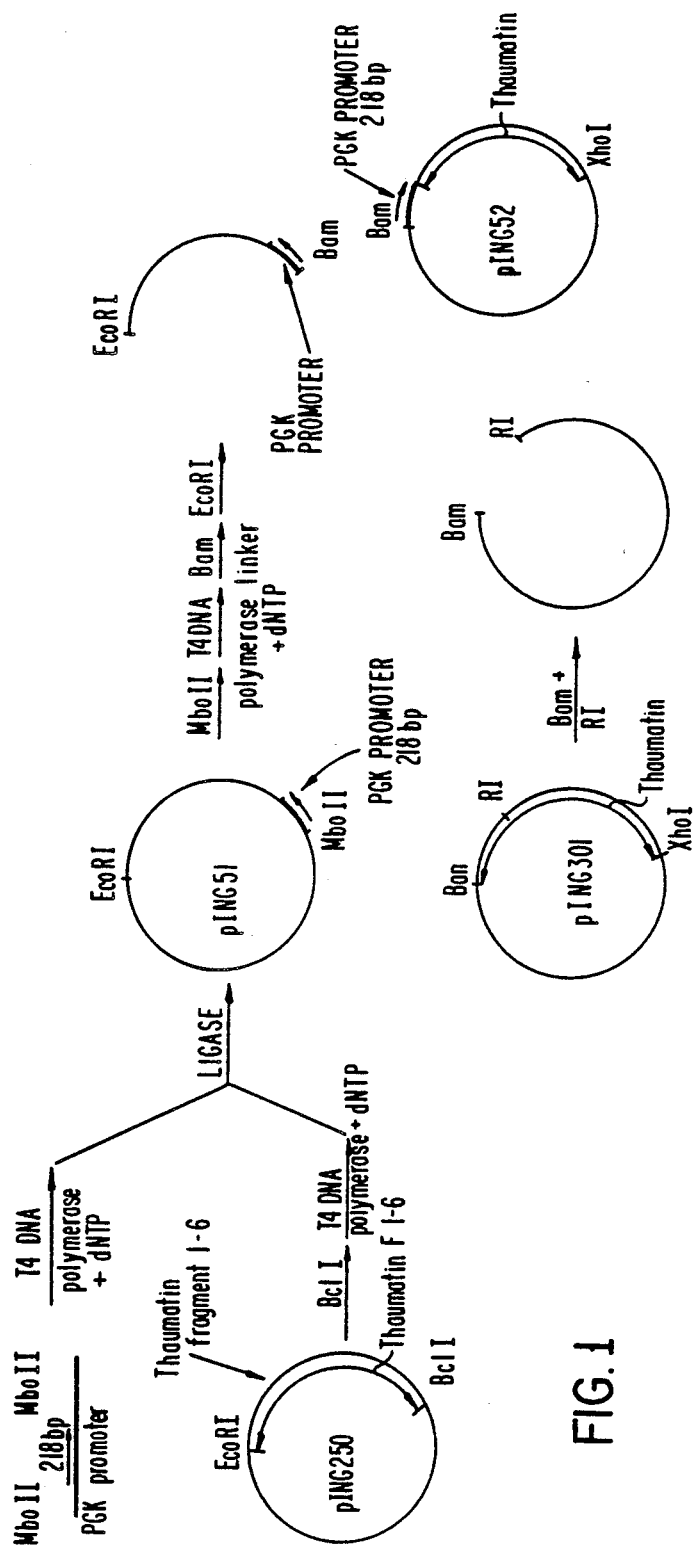
FIG. 1 shows the construction of the plasmid pING52, which carries the shortened PGK promoter.

In the description that follows, a number of terms used in recombinant DNA technology are extensively utilized. In order to provide a clearer and consistent understanding of the specification and claims, including the scope to be given such terms, the following definitions are provided.

Promoter. A DNA sequence generally described as the 5' region of a gene, located proximal to the start codon. At the promoter region transcription or expression of an adjacent gene(s) is initiated.

Polynucleotide molecule. A linear sequence of nucleotides linked together by a backbone consisting of an alternating series of sugar and phosphate residues and as used herein can include DNA and RNA polymers.

Gene. A DNA sequence that contains information for construction of a polypeptide or protein, and as used herein, includes the 5' and 3' ends.

Structural gene. A DNA sequence that is transcribed into messenger RNA that is then translated into a sequence of amino acids characteristic of a specific polypeptide. Typically the first nucleotide of the first translated codon is numbered +1, and the nucleotides are numbered consecutively with positive integers through the translated region of the structural gene and into the 3' untranslated region. The numbering of nucleotides in the promoter and regulatory region 5' to the translated region proceeds consecutively with negative integers with the 5' nucleotide next to the first translated nucleotide being numbered −1.

Heterologous gene. A structural gene that is foreign, i.e. originating from a donor different from the host or a chemically synthesized gene, and can include a donor of a different species from the host. The gene codes for a polypeptide ordinarily not produced by the organism susceptible to transformation by the expression vehicle.

Operably linked. As used herein means that the promoter controls the initiation of the expression of the polypeptide encoded by the structural gene.

Expression. Expression is the process by which a structural gene produces a polypeptide. It involves transcription of the gene into messenger RNA (mRNA) and the translation of such mRNA into polypeptide(s).

Cloning vehicle. A plasmid or phage DNA or other DNA sequence which is able to replicate in a host cell, which is characterized by one or a limited number of endonuclease recognition sites at which such DNA sequences may be cut in a determinable fashion without loss of an essential biological function of the DNA, and which contain a phenotypic selection marker suitable for use in the identification of transformed cells. Markers, for example, are tetracycline resistance or ampicillin resistance. The word "vector" is sometimes used for cloning vehicle.

Expression vehicle. A vehicle similar to a cloning vehicle but which is capable of expressing a given structural gene in a host, normally under control of certain regulatory sequences.

Host. Any organism that is the recipient of a replicable expression vehicle, including bacteria and yeast.

Secretion Signal. A short peptide sequence which contains the information for directing the secretion of proteins fused to the peptide sequence.

DESCRIPTION OF THE PREFERRED EMBODIMENTS

The shortened PGK promoter constitutes the starting point in the development comprising the present invention. The shortened PGK promoter was derived from a 3 Kb HindIII DNA fragment which contains the PGK promoter and the PGK gene. The 5' sequence of the PGK gene is depicted in Hitzeman et al., "The Primary Structure of the *Saccharomyces cerevisae* Gene for 3-Phosphoglycerate Kinase," *Nucleic Acid Research*, 10: 7791–7808 (1982) and in Dobson et al., *Nucleic Acid Research*, 10: 2625–2637 (1982). Both of these are herein incorporated by reference.

As used herein "shortened PGK promoter" is meant to include less than the approximately 1,500 nucleotides of the 5' region of the PGK gene, more specifically, less than 500 base pairs of the proximal end of the 5' region of the PGK gene. Applicants have found that the approximately 536 bp PGK promoter (HaeIII site in the PGK promoter) shown in Dobson et al., *Nucleic Acid Research*, 10:2625–2637, FIG. 1 (1982) and British Patent Application 2150577A had the same effect as the 1.5 Kb PGK promoter, i.e., low level expression of heterologous protein. The number of base pairs comprising the shortened PGK promoter is optimal, and not critical, and is not meant to limit the scope of this invention. Hence, the number of base pairs in a shortened PGK promoter according to this invention may vary, provided however, that the shortened PGK promoter base pair length will comprise the number of base pairs that results in high levels of expression of the structural gene under the control of the shortened PGK promoter. In the preferred embodiment, the number of base pairs comprising the shortened PGK promoter is about 165 to about 404 nucleotides of the proximal end of the 5' region of the PGK gene. Based on applicants' discovery that using a shortened PGK promoter improves the expression of polypeptide under its control, one of skill in the art may employ routine screening to find other shortened PGK promoter sequences for use as a promoter in genetic engineering manipulations.

The shortened PGK promoter can be obtained by isolating the PGK gene from *S. cerevisae*, and then shortening the promoter region enzymatically, chemically or both. However, the practice of this invention is not limited to this source for the shortened PGK promoter. Other sources can include the phosphoglycerate kinase promoter of the genera Kluyveromyces, Aspergillus, Saccharomyces, Pichia or Candida. Further, the PGK promoter may be synthesized de novo; e.g., by manipulation in the laboratory, rather than of natural origin.

In one embodiment of this invention, the shortened PGK promoter is operably linked to a structural gene and the resulting genetic construct is introduced into or forms part of an expression vehicle. The expression vehicle is then utilized to transform an appropriate host cell. The host cell is grown under selected culturing conditions to achieve optimum growth. Although the expression of a structural gene is effected by the shortened PGK promoter, this expression is not necessarily modulated by the glucose concentration in the medium.

In another embodiment of this invention, the shortened PGK promoter is operably linked to a secretion signal which together are operably linked in the correct reading frame to a structural gene. The resulting genetic construct is introduced or made part of an expression vehicle which transforms an appropriate host cell. After proper culturing conditions, the structural gene is expressed, with the added improvement that the expressed polypeptide or protein is secreted into the culture medium. The secreted polypeptide or protein can easily be isolated and purified according to known means. Secretion signals that may be used in this invention include the invertase secretion signal and the pre-thaumatin secretion signal.

In another embodiment of this invention, the secretion signal is used in a method of producing any polypeptide, preferably thaumatin. In this method, a genetic construct is made so that the secretion signal is operable linked to a promoter which together are operably linked in correct reading frame to a structural gene coding for a polypeptide, in particular, thaumatin. The promoters that may be used in this embodiment include the shortened PGK, invertase, alpha factor, CYC, pyruvate kinase, enolase, and any other promoters that are functionally operable in a yeast host. The preferred secretion signals are the invertase secretion signal and the pre-thaumatin secretion signal. An expression vehicle that contains the genetic construct transforms the appropriate yeast host cell. The transformed yeast host cell is grown under selected culturing conditions to produce the polypeptide, which is secreted into the culture medium as a result of the regulatory control of the secretion signal.

In another embodiment of this invention, the shortened PGK promoter is operably linked to a genetic sequence coding for a first polypeptide, and this genetic sequence is operably linked to a second genetic sequence coding for another polypeptide. The expression yields a fusion or precursor protein comprising both the amino acid sequence of the second polypeptide and that of the desired first polypeptide, and containing a selected cleavage site between them, adjacent to the desired amino acid sequence.

The cleavage site is preferably methionine, although the site may be any preferred site known in the art. The desired polypeptide should preferably lack internal cleavage sites corresponding to the actual selected cleavage site. Other known cleavage sites include asn-gly, asp-pro, lys, arg, and lys-arg.

Selective cleavage of the fusion or precursor protein is typically effected outside of the replicative environment of the expression vehicle. In this post-translational step, the fusion or precursor protein is clipped by selective treatment. For example, when methionine is the cleavage site the fusion or precursor protein is treated with cyanogen bromide to clip the desired polypeptide. With other known cleavage sites, the clipping treatment includes hydroxylamine, acid, trypsin, and lys-arg cleavage enzyme.

In a preferred embodiment the desired structural genetic sequence is heterologous to the PGK promoter. In other words, the structural sequence does not naturally occur next to the PGK promoter. In another embodiment the structural sequence is heterologous to the host, i.e., it is not naturally produced by the host.

Methods for preparing fused, operably linked genes and expressing the same in bacteria are known and are shown, for example, in U.S. Pat. No. 4,366,246.

The genetic constructs and methods involved herein can be utilized for expression of the polypeptides in eucaryotic hosts. Eucaryotic hosts may include yeast or filamentous fungi.

In general, plasmid or viral (bacteriophage) vectors containing replicon and control sequences which are derived from species compatible with the host cell are used in connection with these hosts. The vector ordinarily carries a replication site, as well as specific genes that are capable of providing phenotypic selection in transformed cells, typically resistance to antibiotics or ability to synthesize biosynthetic enzymes.

The shortened PGK promoter may be operably linked to a genetic sequence coding for any polypeptide or protein. Examples of such polypeptides or proteins include, but are not limited to, enzymes, hormones, hemoglobin, antibodies, structural proteins, alpha-, beta- and gamma-interferons, interleukins, insulin, and tissue plasminogen activators.

The transformed hosts can be fermented and cultured according to means known in the art to achieve optimal cell growth. The expression of the structural gene product is achieved when the transformed host cells are grown on a fermentable carbon source, such as glucose. Metabolic regulation of the shortened PGK promoter, however, is not necessary according to the process of this invention.

Yeast Plasmid System for Regulating Copy Number

The preferable plasmid constructs according to this invention contain two selectable markers, i.e., (a) leu2-d and (b) a second selectable marker such as TRP1, URA3 or HIS3. These promoters may be repressed by a particular metabolite to inhibit the expression of their gene product. Leucine will inhibit the expression of the leu2-d marker. The plasmid also contains the desired polypeptide to be produced, typically under the control of another promoter, preferably under the control of the shortened PGK promoter.

Thus, according to this invention, the transformed yeast is grown in a medium containing a predetermined amount of leucine and a deficient amount of the second metabolite, e.g., either typtophan, uracil or histidine. By this method, the plasmids are transformed into the yeast with high efficiency, but low copy number, until the leucine is depleted. Upon consumption of the leucine, the leu2-d promoter-operator begins to produce its gene product.

The leu2-d is defective in that it produces only low levels of its gene product, beta-isopropylmalate dehydrogenase (beta-IPMDH). Therefore, to produce sufficient amounts of beta-IPMDH, the plasmid copy number increases in leucine-deficient growth medium, with the consequential increase in the expression of the desired polypeptide (Erhart and Hollenberg, "The Presence of a Defective LEU2 Gene on 2-Micron DNA Recombinant Plasmids of *Saccharomyces cerevisiae* Is Responsible for Curing and High Copy Number," *J. Bacteriol.*, 156: 625-635 (1983)).

When TRP1 or URA3 or any genetic marker not directly involved in the biosynthesis of amino acids other than tryptophan is used as the second selectable marker, acid hydrolyzed casein can be used as the nitrogen source and amino acid supplement. Acid hydrolyzed casein lacks tryptophan and uracil so the medium containing acid hydrolyzed casein still maintains the selection for the TRP1, URA3 or the other non-amino acid markers, e.g. for vitamin or fatty acid biosynthesis. Other amino acid biosynthetic genes may be used as selectable markers in more defined media in which particular amino acids are missing.

When leucine is depleted, the selection for leu2-d expression is then imposed. After the expression phase, the desired polypeptide is recovered from the cells and/or culture medium according to means known in the art.

The following examples further describe the materials and methods used in carrying out the invention. The examples are not intended to limit the invention in any manner.

EXAMPLE 1

Yeast Protein Expression Vector Using A Shortened PGK Promoter

A. The Construction of Thaumatin Expression Vectors

The PGK promoter from *S. cerevisae* was used to express the thaumatin gene in yeast. The PGK gene was isolated from a yeast genomic bank using colony hybridization with synthetic probe (17mer) complementary to the published PGK promoter sequence. (Dobson et al., *Nucleic Acids Research*, 10: 2626–2637 (1982)). A 3 kb HindIII fragment containing the PGK gene was subcloned into pBR322. This plasmid was designated pPGK-p. A 218 bp MboII fragment containing the proximal end of PGK promoter (TATA box, but no UAS sequence) from pPGK-p was blunt-ended by T4 DNA polymerase and ligated to BclI digested and T4 DNA polymerase filled-in pING250 which contains the 5' end of the thaumatin gene (FIG. 1). The resulting plasmid, pING51 contained an MboII site recreated at the 5' end of the PGK promoter but not at the 3' end. This plasmid was redigested with MboII and blunt-ended by treatment with T4 DNA polymerase. After attachment of BamHI linkers at the blunt-ended MboII site, EcoRI was used to remove PGK-thaumatin (portion A) from pING51, and portion A was then joined to BamHI and EcoRI digested pING301 which contains a full-length thaumatin gene. The resulting plasmid, pING52, contained the complete thaumatin sequence 3' to a 218 bp PGK promoter (FIG. 1).

Figure 2:
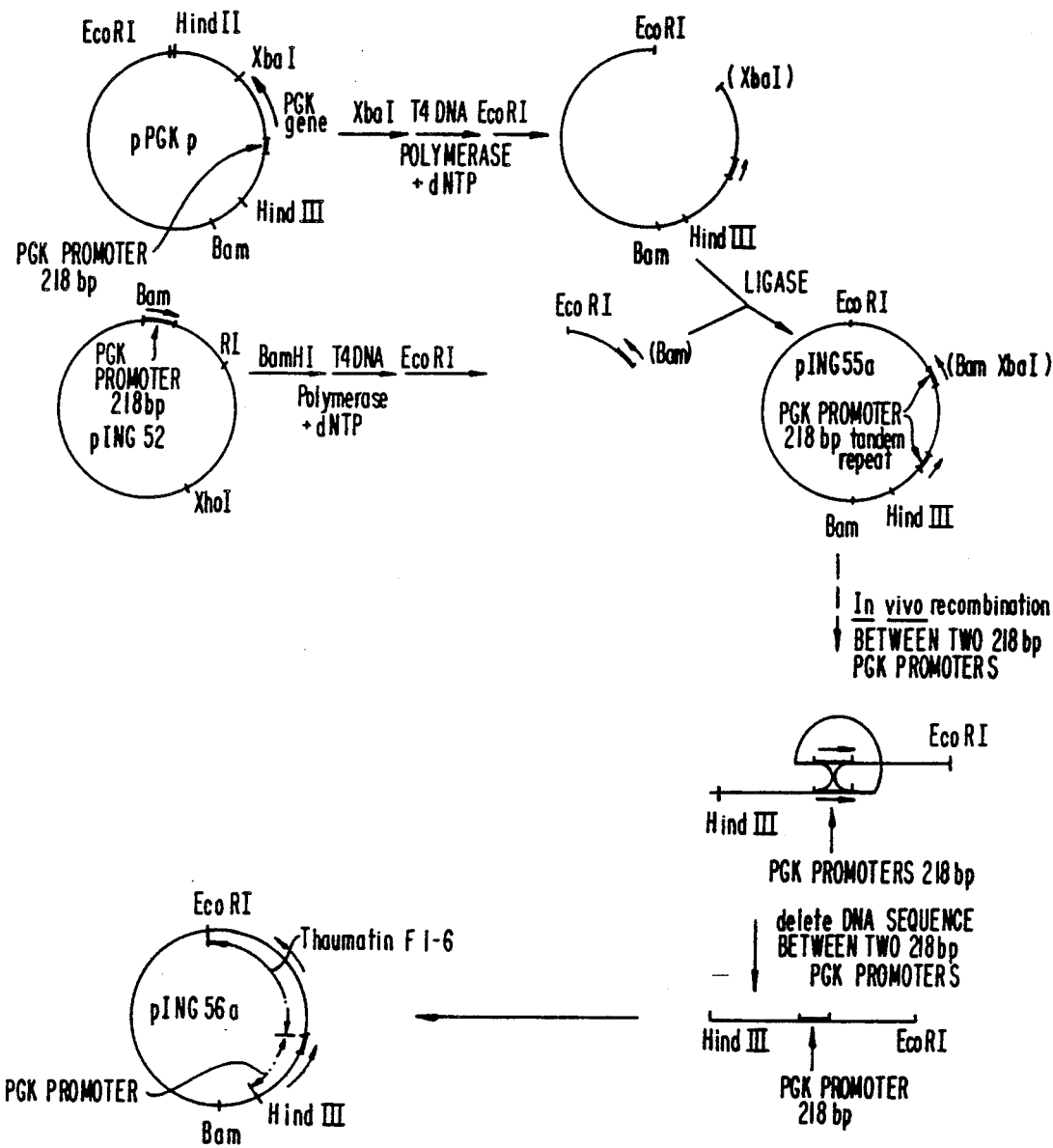
FIG. 2 shows the construction of the plasmid pING-56a, which carries the full length PGK promoter operably linked to portion A of the thaumatin gene.
Figure 3:
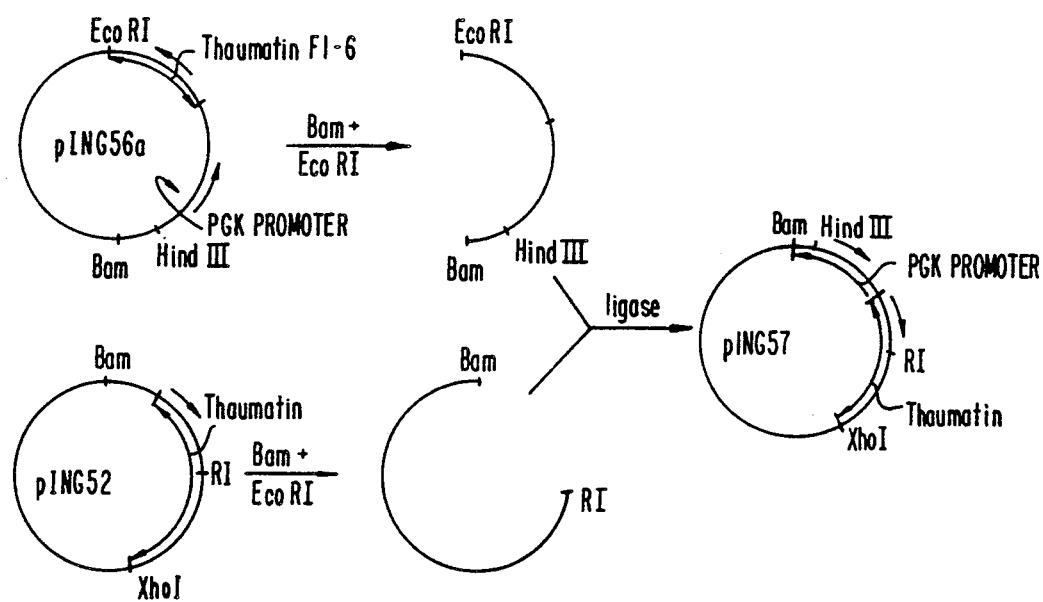
FIG. 3 shows the construction of the plasmid pING57, which carries the full length PGK promoter operably linked to the complete thaumatin gene on a BamHI-XhoI fragment.
Figure 4:
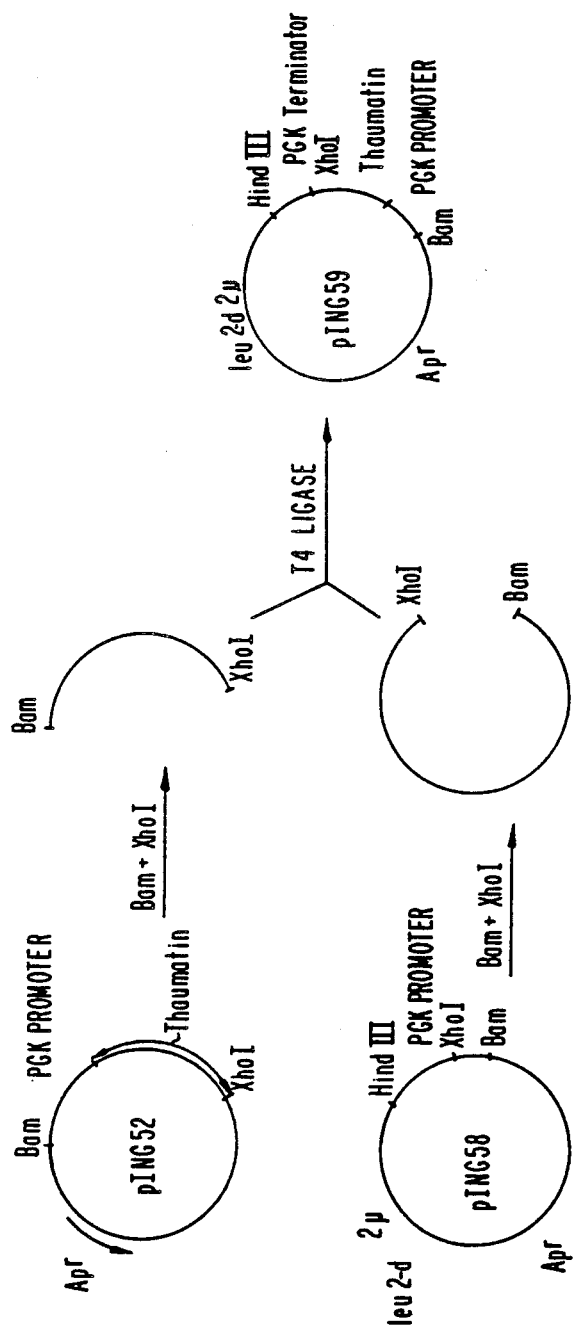
FIG. 4 shows the construction of the plasmid pING59 from the plasmids pING52 and pING58. Plasmid pING59 contains the shortened PGK promoter operably linked to the complete thaumatin gene and also contains the leu2-d selection marker.
Figure 5:
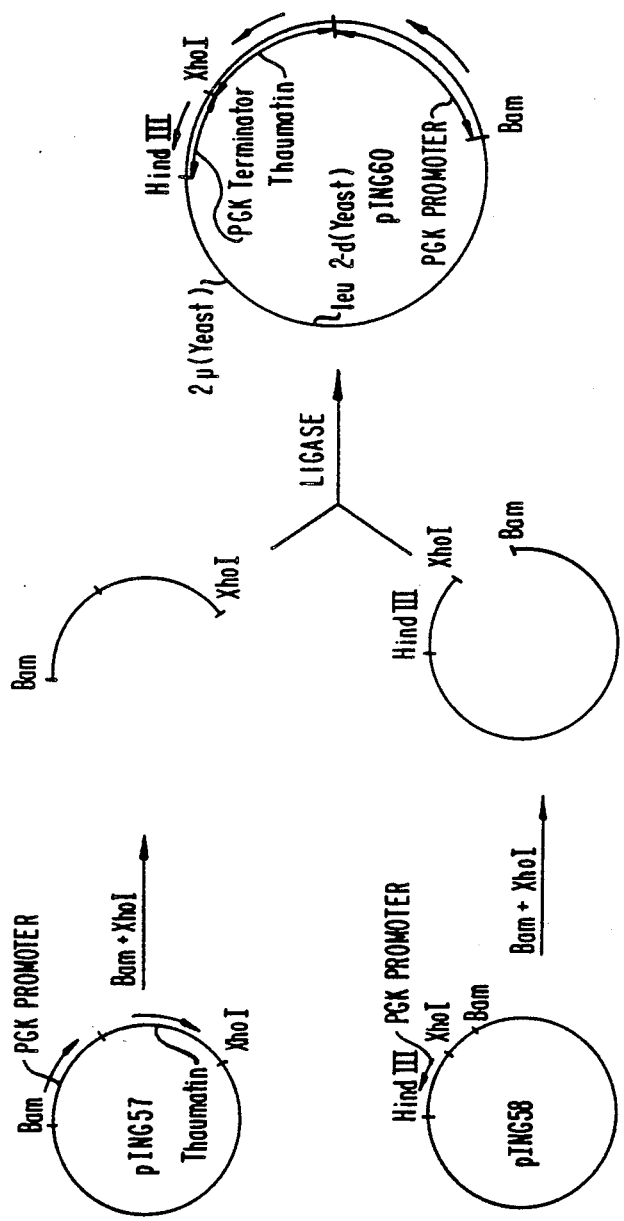
FIG. 5 shows the construction of the plasmid pING60 from the plasmids pING57 and pING58. Plasmid pING60 contains the full length PGK promoter operably linked to the complete thaumatin gene and also contains the leu2-d selection marker.

A full-length PGK promoter-thaumatin gene fusion was constructed by an in vivo recombination technique (FIG. 2) described as follows: The plasmid pING52 was digested with BamHI, filled in with T4 DNA polymerase, then digested with EcoRI to generate a PGK promoter-thaumatin (portion A) fragment which contained a blunt-end at the 5' position and an EcoRI sticky end at the 3' end. This fragment was then joined to pPGK-p, which had been digested with XbaI, treated with T4 DNA polymerase to fill in the ends, and digested with EcoRI, to form pING55a. Since the XbaI site was in PGK structural gene and the EcoRI site was further downstream in the PGK gene, the joined 218 bp PGK promoter became a tandem duplication of the same 218 bp sequence in the upstream intact PGK promoter. A deletion generated between these two tandemly duplicated regions through in vivo recombination in *E. coli* placed the intact PGK promoter immediately upstream from the 5' end of the thaumatin gene. A representative clone was designated pING56a. Because only portion A of the thaumatin gene was in pING56a, the PGK-thaumatin (portion A) was removed from pING56a by a BamHI-EcoRI double digestion and joined to the same restriction sites in pING52 (FIG. 3). The resulting plasmid, pING57 contained the complete PGK promoter and thaumatin gene on a BamHI-XhoI fragment. This BamHI-XhoI fragment from either pING52 or pING57 was then ligated to the same restriction sites in pING58, an *E. coli*-yeast shuttle vector, resulting in the PGK terminator being positioned downstream from the thaumatin gene. The final products, pING59 and pING60, contain the 218 bp and the complete PGK promoter-thaumatin-PGK terminator complexes, respectively (FIGS. 4 and 5).

Figure 6:
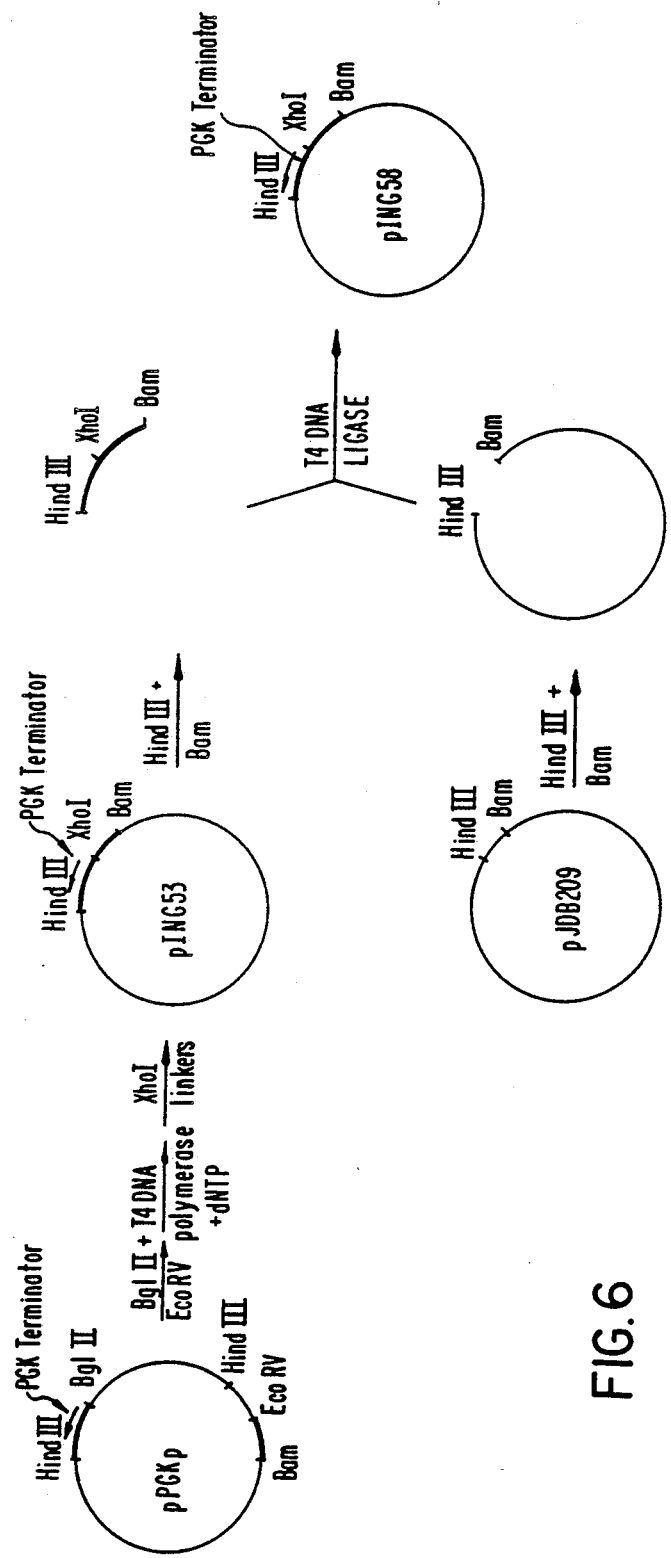
FIG. 6 shows the construction of the plasmid pING58, which contains the PGK terminator.

Plasmid pING58 was constructed as follows (FIG. 6): The plasmid pPGK-p was digested with BolII and EcoRV and blunt-ended by treatment with T4 DNA polymerase. XhoI linkers were attached, and the plasmid was religated and transformed into MC1061 (Casadaban and Cohen, "Analysis of gene control signals by DNA fusion and cloning in *Escherichia coli*", *J. Mol. Biol.*, 138: 179–207 (1980)) to generate pING53. In pING53, the PGK terminator was located between the XhoI and HindIII sites. A BamHI-HindIII fragment containing the PGK terminator and 190 bp of pBR322 DNA was then joined to the yeast-*E. coli* shuttle vector, pJDB209 (Beggs, J., "Multicopy Yeast Plasmid Vectors" in *Molecular Genetics in Yeast*, von Wettstein, et al., eds. (Copenhagen 1981)), at the BamHI and HindIII sites to create pING58.

B. Expression of Thaumatin Gene in Yeast by PING59 or pING60

Plasmid pING59 or pING60 was transformed into yeast strain AH22, and Leu+ transformants were selected on SD-leu agar. Properties of pING59/AH22 and pING60/AH22 were compared as shown in the following table:

TABLE I

|  | pING59/AH22 | pING60/AH22 |
|---|---|---|
| 1. Time required for transformants to appear | 4 days | 10 days |
| 2. Thaumatin production (% of total protein): | | |
| Less than 20 ml culture | 20% | 10% |
| Larger than 100 ml | 20% | 0% |

The comparison clearly shows a shortened PGK promoter in pING59 is a much better thaumatin expression vector than pING60 which contains the full-length PGK promoter.

EXAMPLE 2

Figure 7:
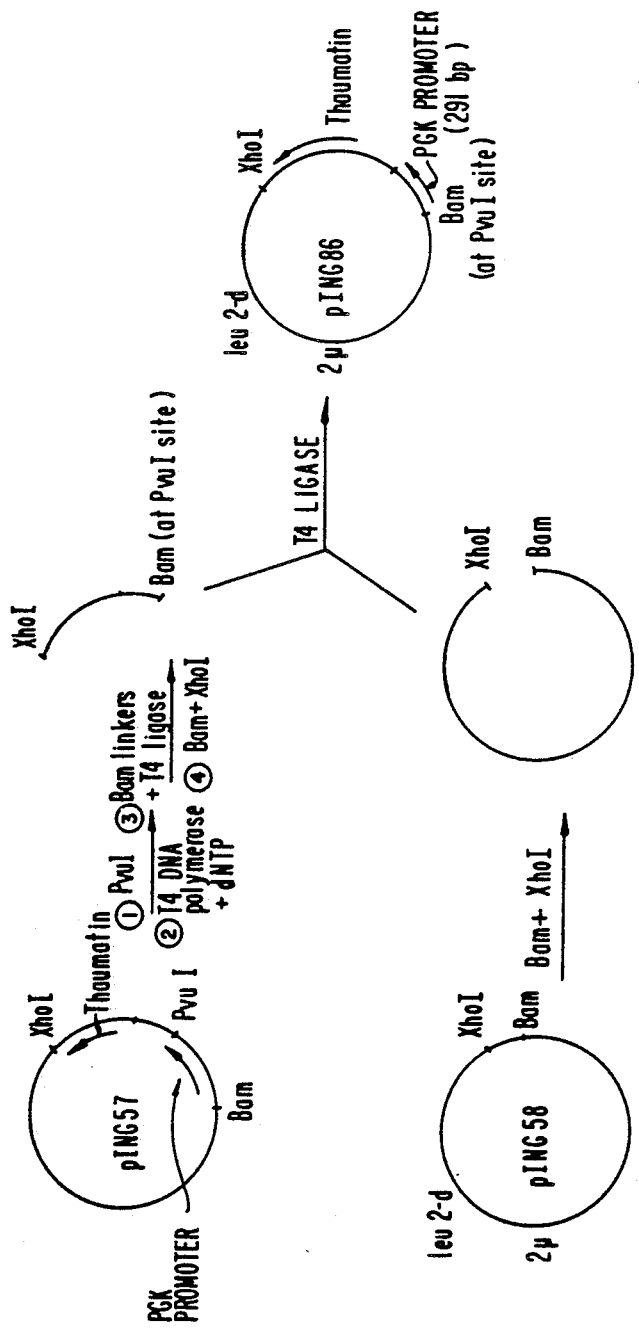
FIG. 7 shows the construction of plasmid pING86 which contains the 291 bp PGK promoter 5' to the thaumatin gene.

Comparison of Thaumatin Expression in a Yeast Expression Vector with Various Lengths of PGK Promoter A. Construction of a plasmid containing a 291 bp PGK promoter-thaumatin fusion (FIG. 7)

Plasmid pING57 which contains the full length PGK promoter-thaumatin fusion was digested with PvuI, which cleaves at −291 of the PGK promoter, and blunt-ended by treatment with T4 DNA polymerase. After attachment of BamHI linkers at the blunt-ended PvuI site, BamHI and XhoI were used to remove the PGK (291bp)-thaumatin fragment from pING57, and this BamHI-XhoI fragment was then joined to BamHI and XhoI digested pING58 to form pING86. Plasmid pING86 contains a 291 bp PGK promoter 5' to the thaumatin gene.

Figure 8:
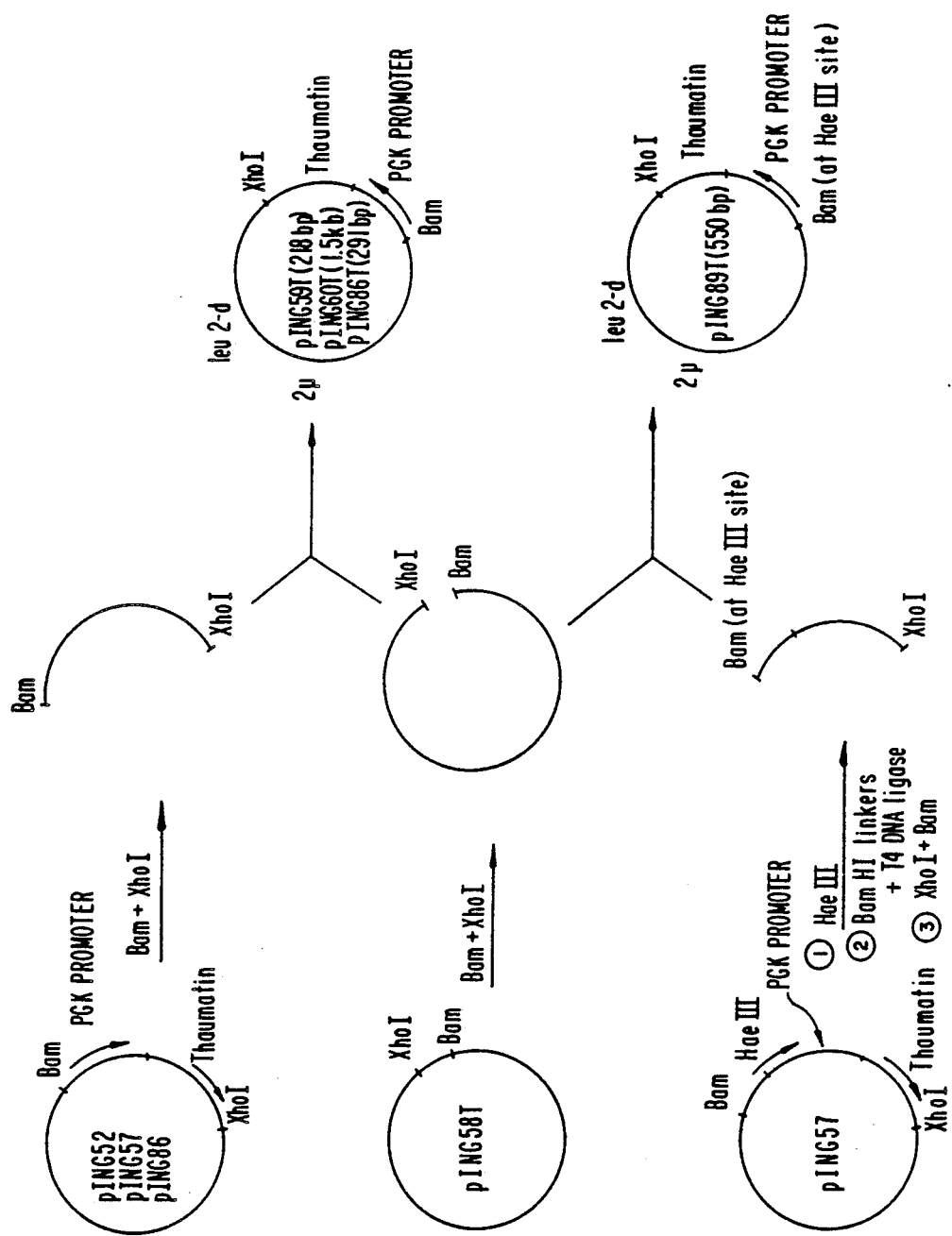
FIG. 8 shows the construction of yeast expression plasmids containing the following: a 218 bp PGK promoter-thaumatin fusion (pING59T), a 291 bp PGK promoter-thaumatin fusion (pING86T), a 536 bp PGK promoter-thaumatin fusion (pING89T), and a 1.5 kb PGK promoter-thaumatin fusion (pING60T).

B. Construction of a yeast expression vector containing a 536 bp PGK promoter-thaumatin fusion (FIG. 8)

Plasmid pING57 was digested with HaeIII, which cleaves at −536 of the PGK promoter, and BamHI linkers were attached. (This 536 bp PGK promoter corresponds to the PGK promoter shown in British Patent Application 2150577A.) BamHI and XhoI were then used to remove the PGK (536bp)-thaumatin fragment from pING57, and this BamHI-XhoI fragment was then joined to BamHI and XhoI digested pING58T to form pING89T.

C. Construction of a yeast expression vector with either a 218bp, 291bp, or 1500bp PGK promoter-thaumatin fusion (FIG. 8)

Plasmids pING52, pING57 and pING86 were digested with BamHI and XhoI. Each BamHI-XhoI fragment containing a PGK promoter-thaumatin fusion was cloned onto pING58T which was digested with BamHI and XhoI. The resulting plasmids pING59T, pING60T and pING86T contain 218bp, 1500bp and 291bp PGK promoters, respectively.

D. Expression of PGK promoter-thaumatin fusion of various lengths

Expression of PGK promoter-thaumatin fusion of various lengths in yeast plasmids pING59T, pING60T, pING86T and pING89T were transformed into yeast strain BB29-1C (MATa, leu2-3, 2-112, trp1) individually as described in Example 2, section C. One transformant from each transformation was inoculated into liquid SD+1% CAA medium. Each starter culture (at klett 200, red filter) was used to inoculate, at a 1/100 dilution, a 225 ml SD-leu media. After 48 hours incubation at 30° C., cells were harvested, and the expression of thaumatin by the yeast cells containing the various plasmids was compared. Yeast cells containing pING59T and pING86T produced approximately the same amount of thaumatin, whereas yeast cells containing pING60T and pING89T produced much less thaumatin. The comparison shows that the 291 bp and 218 bp promoters have the same high level of thaumatin expression, and that the 536bp PGK promoter has the same effect as a full-length PGK promoter.

E. Expression of Thaumatin with PGK promoter of Lengths 536bp, 404bp, 291bp, 218bp, 195bp or 165bp To determine the length of PGK promoter that will maintain a high level of thaumatin expression various lengths of PGK promoter were used to express the thaumatin gene in yeast There are several restriction sites in the PGK promoter (British Patent Application, 2,150,577A). Using A in the translation initiator ATG as +1, a HaeIII site is located at position −536, 5' to the UAS sequence, and a PssI site is located at position −404 inside the UAS sequence. A PvuI site at position −291, a MboII site at position −218, a BstXI site at position −195, and a MnlI site at position −165 are all located between the UAS sequence and the TATA box. Digestion with these six restriction enzymes generated PGK promoters with 536bp, 404bp, 291bp, 218bp, 195bp and 165bp, respectively. DNA fragments containing various lengths of PGK promoter fused to the thaumatin gene (YP406) were cloned into a yeast- *E.*

*coli* shuttle vector, pING58. The derived plasmids were each used to transform yeast strain BB25-1d (MATa, leu2-3, 2-112), and Leu + transformants were selected on SD-leu plates. Transformants appeared after incubation at 30° C. for 4 days with all of the plasmids used except the plasmid containing the 536 bp PGK promoter which took 10 days Leu+ transformants with each plasmid were inoculated into YPD liquid media. Each YPD starter culture (at Klett 200, red filter) was used to inoculate 200 mls of SD-leu medium at a 1/100 dilution. After 48 hour incubation with shaking (250 rpm) at 30° C., cells were harvested and broken with glass beads. The aqueous insoluble fraction was extracted with boiling 1% SDS. The amounts of thaumatin expressed in yeast cells by various lengths of PGK promoter were compared by running these extracts on SDS-PAGE. PGK promoters with lengths of 404bp, 291bp, 218bp, 195bp or 165bp directed the expression of thaumatin in yeast at about the same level (approximately 10–20% of the total cellular protein) whereas the 536bp PGK promoter expressed thaumatin at a very low level (less than 1% of the total cellular protein).

EXAMPLE 3

A Yeast Plasmid System in Which the Copy Number Is Regulated

A. Construction of pING58T

The precursor plasmid of pING58T was pING58 whose construction is described in Example 1. To summarize, pING58 is an *E. coli-S. cerevisae* shuttle vector which contains most of the sequences of the bacterial vector pAT153, including the beta-lactamase gene (bla) for ampicillin resistance and the bacterial origin of replication (oriB) from pBR322 for selection and amplification in bacteria. For replication in yeast, pING58 contains the origin of replication (oriY) and another cis-acting sequence (REP3) from the yeast endogenous 2-micron plasmid. In addition, it contains leu2-d, a version of the yeast LEU2 gene which lacks most of the promoter region leading to lower levels of transcription. The low level of transcription from each copy selects for a high copy number per cell for leucine-less growth pING58 also contains the yeast PGK terminator which is used to terminate transcription of genes inserted at its 5' side.

pING58 was digested with the restriction enzyme HindIII, and the resulting single-stranded overhanging 5'-ends were filled in by T4 DNA polymerase to form double-stranded "blunt" ends. These blunt ends were subsequently treated with calf intestinal phosphatase to remove the 5' terminal phosphates. This prevents self-ligation of the precursor plasmid if it does not incorporate another fragment.

The fragment to be incorporated into pING58 was an 850 bp fragment containing the TRP1 gene from *S. cerevisae* (Tschumper, G. and J. Carbon, "Sequence of a yeast DNA fragment containing a chromosomal replicator and the TRP1 gene," Gene, 10: 157–166 (1980)). This fragment was prepared by digesting pING63 with restriction enzymes BglII and EcoRI. pING63 is an *E. coli* vector that contains the yeast TRP1 gene as a BglII-EcoRI restriction fragment with a BglII linker fragment, replacing the BamHI-EcoRI restriction fragment in pBR322. The two fragments resulting from cleavage of pING63 were also made to have blunt ends by the action of T4 DNA polymerase. To lower the frequency of remaining intact pING63 molecules from transforming bacteria in a subsequent step, the pING63 fragments were treated with restriction enzyme PvuI.

The pING58 and pING63 fragments were mixed together in a weight/weight ratio of approximately 1:3=pING58:pING63. The final DNA concentration was approximately 20 ug/ml. After ligating with T4 DNA ligase for about 48 hours at 12° C., the mixture was used to transform E. coli strain MC1061 to ampicillin resistance. Of eleven transformants, one carried two XbaI restriction fragments. The smaller 1.2 kb fragment suggests that the putative TRP1 insert is oriented with the 3' end of TRP1 adjacent to the 2-micron sequences and the 5' end adjacent to the PGK terminator of pING58.

Figure 9:
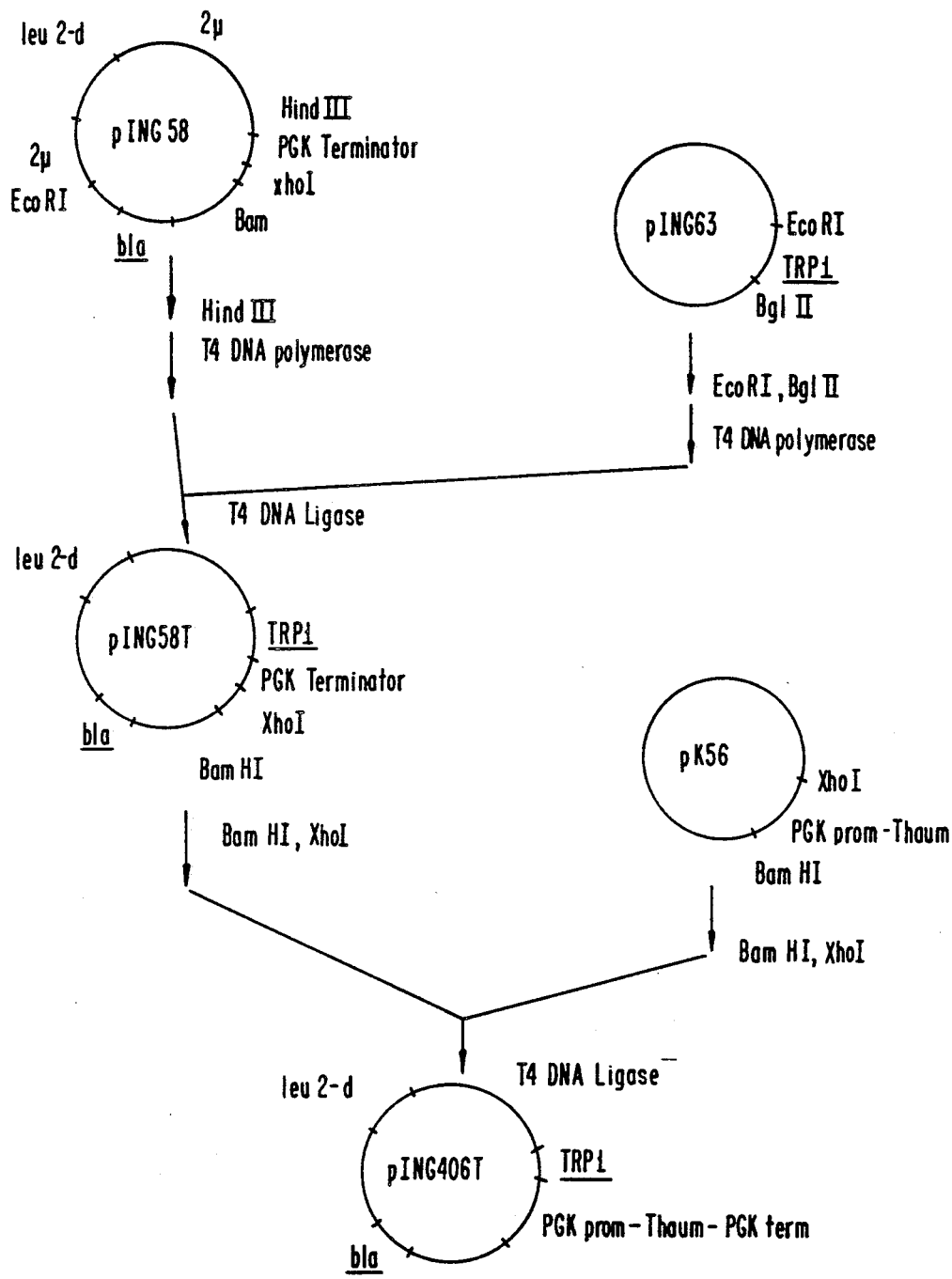
FIG. 9 shows the construction of the plasmid pING406T, which contains the shortened PGK promoter operably linked to the complete thaumatin gene and which also contains the leu2-d and TRP1 selection markers.

This plasmid, called pING58T (FIG. 9), could transform our yeast strain BB28-ld (MATa his4-519 leu2-3, 2-112 trp1) to a Trp+ phenotype, and furthermore these Trp+ transformants were also Leu+. This indicates that in addition to the inserted TRP1 gene, pING58T also contains the functional leu2-d gene from pING58.

B. Construction of pING406T

To test the utility of pING58T as a plasmid for regulating the expression of a foreign gene, a DNA fragment, bounded by BamHI and XhoI sites, and containing the shortened PGK promoter from yeast and a synthesized sequence encoding the sweet protein thaumatin, was inserted into pING58T by replacing a BamHI-XhoI fragment in front of the PGK terminator. The resulting plasmid was named pING406T (FIG. 7).

C. pING406T in Yeast Is Regulated for Thaumatin Expression pING406T was used to transform yeast strain BB28-ld to TRP+ by selecting for growth on SD agar (2% glucose, 0.67% Difco yeast nitrogen base, 2% agar) supplemented with 1% acid hydrolyzed casamino acids (CAA). One of the transformant colonies was inoculated into liquid SD+1% CAA media. This starter culture was used to inoculate, at a 1/30 dilution, three 550 ml cultures with different media conditions: A) SD-leu; B) SD+1% CAA; and C) SD+1% CAA+300 mg leucine/liter. Only the cells grown in SD-leu produced significant amounts of thaumatin, while cells grown in media B or C produced little, if any. This indicates that selection for growth without tryptophan does not result in a high level of thaumatin production. Selection for growth without leucine, however, does lead to high level thaumatin production.

Growth without tryptophan selects only for a moderate number of plasmid copies per cell, not enough to significantly express thaumatin. Growth without leucine, though, selects for a much higher copy number because leu2-d is somewhat defective for transcribing LEU2 message. This second selection increases the plasmid copy number, which increases LEU2 function. This copy number increase also results in significant thaumatin production.

EXAMPLE 4

Figure 10:
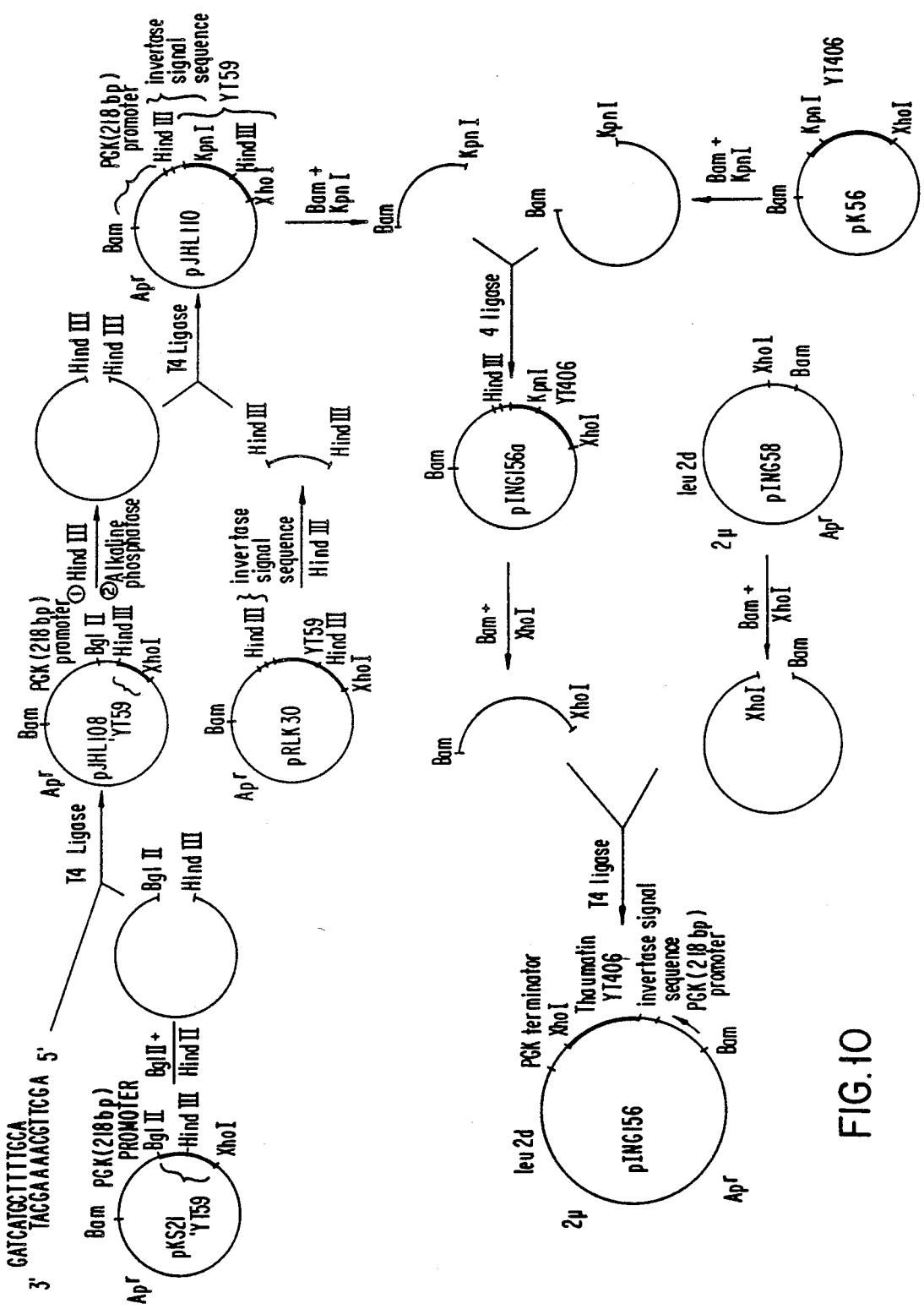
FIG. 10 shows the construction of a shortened PGK promoter (218 bp)—invertase signal sequence—thaumatin YT406 fusion on a high copy-number yeast—*Eschericia coli* shuttle vector, pING156.

Secretion of Thaumatin Directed by Yeast PGK Promoter and Invertase Signal Sequence In large scale fermentation, the most widely used carbon source is glucose. Since expression from the yeast invertase promoter is repressed at high concentrations of glucose, the yeast PGK promoter, which is a strong, glucose inducible promoter, was used to replace the invertase promoter. The construction of a PGK(218bp) promoter-invertase signal sequence-thaumatin YT406 fusion on a high copy-number (~200 copies/cell) yeast-E. coli shuttle vector is outlined in FIG. 10. The final plasmid pING156 was transformed into yeast strain BB33-1C (MATa ura3 leu2), and Leu+ transformants were selected. Leu+ transformants began to appear on the SD-leu plate after incubation at 30+ C. for 2-3 weeks. Among the Leu+ transformants an average of one out of eight secreted thaumatin into the growth medium at a level of 600-1000 ug/l.

Figure 11:
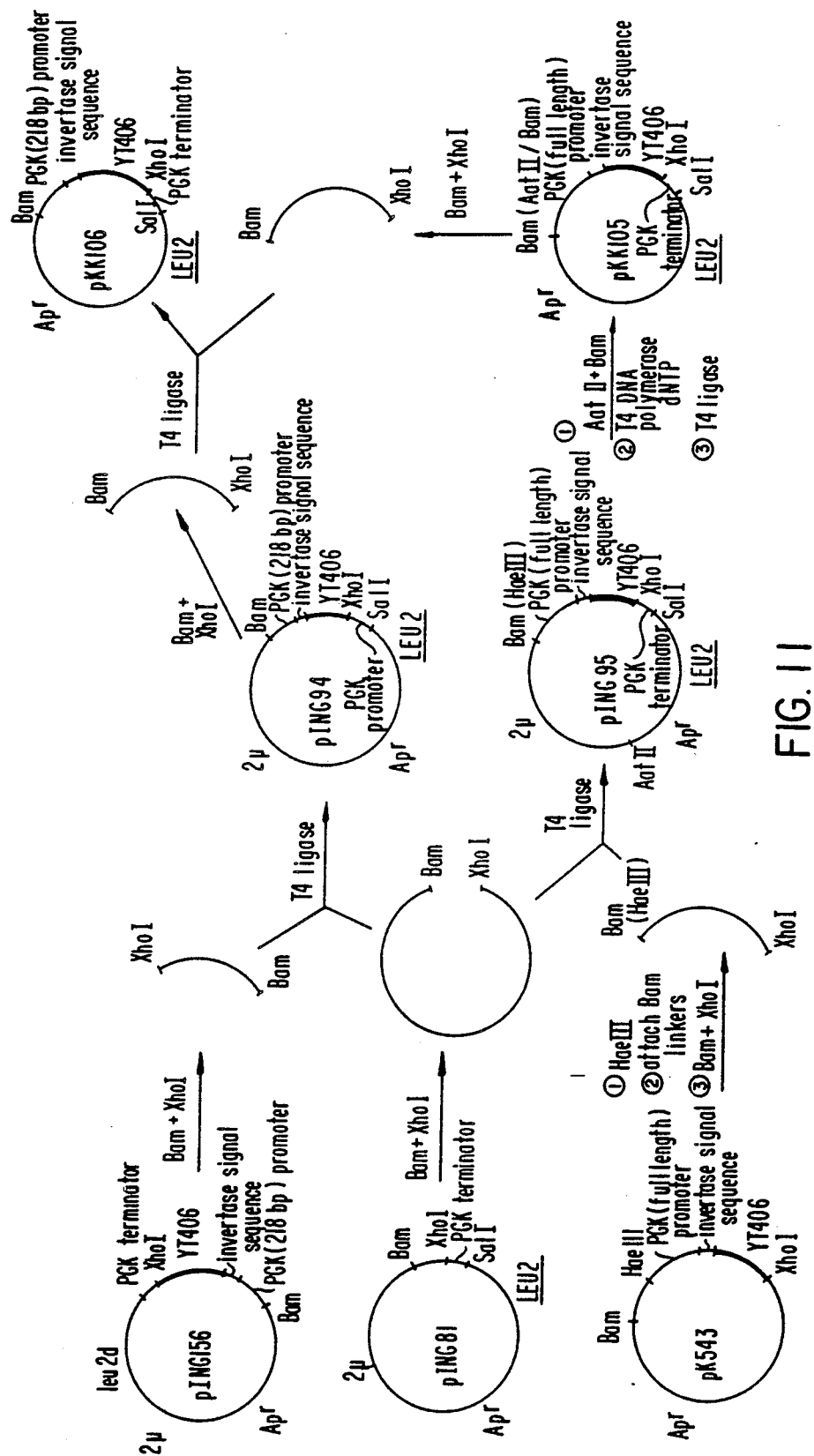
FIG. 11 shows the construction of plasmids pING94 and pING95 containing, respectively, the 218 bp and the 536 bp (full length) PGK promoter-invertase a medium copy number yeast—*E. coli* shuttle vector.

The 218bp and the 536bp (full length) PGK promoter-invertase signal sequence-thaumatin YT406 fusions were also cloned into a medium copy number (~20 copies/cell) yeast-E. coli shuttle vector to generate pING94 and pING95, respectively (FIG. 11). Plasmids pING94 and pING95 were used to transform BB33-1C separately. Leu+ transformants appeared after incubation at 30° C. for 2 days. Four transformants from either BB33-1C [pING94] or BB33-1C [pING95] were picked and grown in SD-leu broth. Every transformant secreted YT406 into the growth medium at a level of 200 to 400 ug/l.

To study the secretion of single copy transformants, integration vectors were constructed by deleting the yeast 2u sequences from pING94 and pING95 to generate pKK106 and pKK105, respectively. About one-half of the Leu+ transformants of BB33-1c (which appeared after 5-6 days) with either pKK105 or pKK106 also secreted YT406 into the growth medium at a level of 200 to 400 ug/l. The non-secreting transformants are presumed to be corrected only for the defective leu2 gene of BB33-1c.

EXAMPLE 5

Secretion of Thaumatin Directed by Yeast PGK Promoter (218bp) and Pre-Thaumatin Signal Sequence Thaumatin is a secreted plant protein. Based on a cDNA derived thaumatin protein sequence, there is a 22 amino acid pre-thaumatin sequence which is not present in the mature thaumatin. This 22 amino acid sequence has the basic characteristics of secretion signal sequences and presumably directs the secretion of thaumatin. To test whether this 22 amino acid can actually direct the secretion of thaumatin in yeast, a yeast PGK(218bp) promoter-pre-thaumatin signal sequence-thaumatin(YT406) fusion was constructed.

A synthetic DNA fragment coding for the 22 amino acid signal sequence using yeast preference codons was chemically synthesized and assembled:

<u>ATG</u> GCT GCT ACT ACT TGT TTC TTC TTC TTA TTC CCA TTT
Met Ala Ala Thr Thr Cys phe phe phe Leu phe pro phe <u>    SstI    </u>                                      <u>    PstI    </u>
TTG AGCT CTA TTG TTG ACT TTG TCT AGA GCC TCGAG
Leu      Leu Leu Leu Thr Leu Ser Arg Ala This synthetic fragment has 2 unique features:

(1) To facilitate DNA cloning, four extra basic pairs (AGCT) were inserted between codons 14 & 15 to create a SstI restriction site. Upon digestion with SstI, chewing back with T4 DNA polymerase and religation with T4 ligase, these four base pairs can be deleted to resume the correct pre-thaumatin sequence.

Figure 12:
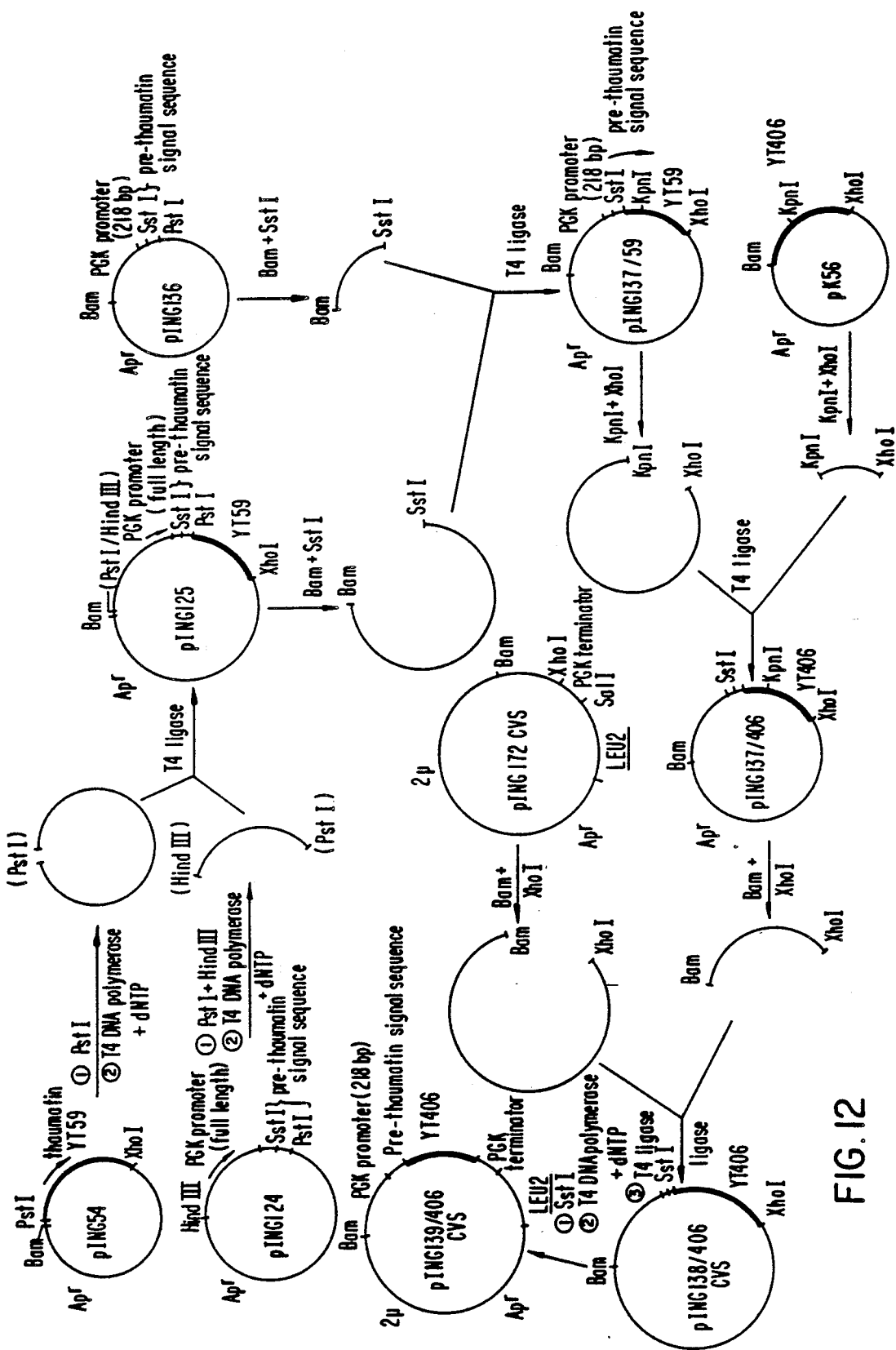
FIG. 12 shows the construction of a shortened (218 bp) PGK promoter—pre-thaumatin signal sequence—thaumatin YT406 fusion on a medium copy number yeast—*E. coli* shuttle vector, pING139CVS.

(2) A PstI site was designed at the 3'-end of the fragment to join to the thaumatin gene or other heterologous genes with the correct junction. Plasmids pING124 and pING136 contain this DNA fragment fused to the 3'-end of the full length or 218 bp PGK promoter, respectively. Constructions of a PGK(218 bp) promoter-pre-thaumatin signal sequence-thaumatin YT406 fusion on a medium copy number yeast-*E. coli* shuttle vector are diagrammed in FIG. 12. Transformants were obtained when pING139CVS was used to transform BB33-1c. BB33-1c[pING139CVS] secreted YT406 into the growth medium at a level of 400 to 500 ug/l.

Although the instant disclosure sets forth all essential information in connection with the invention, the numerous publications cited herein may be of assistance in understanding the background of the invention and the state of the art. Accordingly, all of the publications cited are hereby incorporated by reference into the patent disclosure. Moreover, the foregoing invention has been described in some detail by way of illustration and example for purposes of clarity and understanding. It will be obvious that certain changes and modifications may be practiced within the scope of the invention, as limited only by the scope of the appended claims.

What is claimed is:

1. A shortened promoter of the PGK gene, wherein said promoter comprises about 165 to about 404 base pairs of the proximal end of the 5' region of the PGK gene, said promoter providing improved expression of polypeptides under its control as compared to said expression provided by the full-length PGK promoter.

2. A polynucleotide molecule expressible in a given host cell comprising a sequence of the shortened PGK promoter of claim 1 operably linked to a structural gene.

3. An expression vehicle for use in recombinant DNA which is capable of replicating and expressing genetic information and having the promoter base pair sequence length of about 165 to about 404 base pairs of the proximal end of the 5' region of the PGK gene, said promoter controlling the expression of a structural polypeptide.

4. A expression vehicle for use in recombinant DNA which is capable of replicating and expressing genetic information and having the promoter base pair sequence length of about 165 to about 404 base pairs of the proximal end of the 5' region of the PGK gene operably linked to a secretion signal, said promoter and secretion signal controlling the expression and secretion of a structural polypeptide.

5. The expression vehicle of claim 4 wherein said secretion signal is selected from the invertase secretion signal and the pre-thaumatin secretion signal.

6. A host cell transformed by the expression vehicle of claim 3 or 4.

7. A method of producing a desired polypeptide comprising culturing a host cell transformed by the expression vehicle of claim 3 under conditions selected to produce said desired polypeptide.

8. A method of producing a desired polypeptide comprising culturing a host cell transformed by an expression vehicle having the promoter base pair sequence length of about 165 to about 404 base pairs of the proximal end of the 5' region of the PGK gene operably linked to a secretion signal, said promoter and secretion signal controlling the expression and secretion of said polypeptide, under conditions selected to produce and secrete said polypeptide into the culture medium.

9. The method of claim 8 wherein said polypeptide is thaumatin.

10. The method of claim 8 wherein said secretion signal is the pre-thaumatin secretion signal.

11. A method for increasing the expression of a heterologous polypeptide in transformed yeast comprising culturing yeast transformed with an expression vehicle that comprises:
   (i) a first selectable marker;
   (ii) a second selectable marker, leu2-d; and
   (iii) a gene that encodes a heterologous polypeptide under the control of the promoter of claim 1 that is expressed by said transformed yeast,
   in a culture medium containing a deficient amount of the metabolite of the first selectable marker and a predetermined amount of leucine to obviate the requirement for expression of the said second marker, leu2-d, for a time sufficient to allow efficient transformation and growth of said transformed yeast, and upon depletion of leucine, required expression of leu2-d selects for increased plasmid copy number which concomitantly results in increased expression of said heterologous polypeptide.

12. The method according to claim 11 wherein said first selectable marker is TRP1, URA3 and HIS3.

* * * * *

UNITED STATES PATENT AND TRADEMARK OFFICE
CERTIFICATE OF CORRECTION

PATENT NO. : 5,104,795
DATED : April 14, 1992
INVENTOR(S) : Lee et al

It is certified that error appears in the above-indentified patent and that said Letters Patent is hereby corrected as shown below:

On the title page: Item [56] "Ieskin" should read --Teskin --.

Signed and Sealed this

Twenty-eighth Day of December, 1993

Attest:

BRUCE LEHMAN

Attesting Officer

Commissioner of Patents and Trademarks